US008876748B2

(12) United States Patent
Nakamura

(10) Patent No.: US 8,876,748 B2
(45) Date of Patent: Nov. 4, 2014

(54) COVER FOR GAS MIST PRESSURE BATH

(75) Inventor: Shoichi Nakamura, Higashichikuma-gun (JP)

(73) Assignees: ACP Japan Co., Ltd., Tokyo (JP); Shoichi Nakamura, Higashichikuma-gun, Nagano (JP)

( * ) Notice: Subject to any disclaimer, the term of this patent is extended or adjusted under 35 U.S.C. 154(b) by 602 days.

(21) Appl. No.: 12/736,423

(22) PCT Filed: Dec. 25, 2009

(86) PCT No.: PCT/JP2009/071534
§ 371 (c)(1), (2), (4) Date: Oct. 7, 2010

(87) PCT Pub. No.: WO2010/074198
PCT Pub. Date: Jul. 1, 2010

(65) Prior Publication Data

US 2011/0028888 A1 Feb. 3, 2011

(30) Foreign Application Priority Data

Dec. 26, 2008 (JP) ............................ 2008-009181 U
Dec. 26, 2008 (JP) ............................ 2008-009182 U
Mar. 10, 2009 (JP) ............................ 2009-001398 U
Mar. 10, 2009 (JP) ............................ 2009-001399 U

(51) Int. Cl.
*A61M 37/00* (2006.01)
*A61H 35/00* (2006.01)
*A61H 33/14* (2006.01)

(52) U.S. Cl.
CPC .......... *A61H 35/00* (2013.01); *A61H 2201/165* (2013.01); *A61H 2201/0207* (2013.01); *A61H 2033/143* (2013.01); *A61H 2033/145* (2013.01)
USPC ............................................... 604/24; 604/23

(58) Field of Classification Search
USPC ..................................................... 604/23–24
See application file for complete search history.

(56) References Cited

U.S. PATENT DOCUMENTS 2,906,266 A * 9/1959 Lagodmos ................... 604/341
3,874,387 A * 4/1975 Barbieri .......................... 602/53
4,224,941 A * 9/1980 Stivala ............................ 604/23
5,810,795 A * 9/1998 Westwood ................... 604/305

(Continued)

FOREIGN PATENT DOCUMENTS

| | | |
|---|---|---|
| JP | S61-217132 | 9/1986 |
| JP | 2005-058745 | 3/2005 |
| JP | 3144718 U | 9/2008 |
| WO | WO2008/047829 | 4/2008 |

*Primary Examiner* — Edelmira Bosques
(74) *Attorney, Agent, or Firm* — Manabu Kanesaka

(57) ABSTRACT

A cover for gas mist pressure bath includes a living-body cover member having an extension part extending from substantially center part of the living-body cover member, an adhesive part adhering the cover member to the skin and the mucous membrane of the living-body, a gas mist supply port for introducing the gas mist into the cover member for gas mist pressure bath, an outlet for exhausting air, the gas mist or the mixed gas sealed in the cover member for the gas mist pressure bath and controlling amounts of the gas, a fixing member fixing the cover member on the living-body, including a pair of belts extending from an edge of the adhesive part and a pair of belt stoppers adjusting the pair of belts, and a constricting ring pressurizing an inside of the living-body cover member to carry out pressurization.

4 Claims, 12 Drawing Sheets

(56) References Cited

U.S. PATENT DOCUMENTS

| | | | | |
|---|---|---|---|---|
| 6,638,270 | B2 * | 10/2003 | Johnson | 604/890.1 |
| 6,652,479 | B2 * | 11/2003 | Rasor et al. | 604/23 |
| 2002/0156416 | A1 * | 10/2002 | Stenzler | 604/23 |
| 2005/0137521 | A1 * | 6/2005 | Stenzler | 604/23 |

* cited by examiner

COVER FOR GAS MIST PRESSURE BATH

RELATED APPLICATIONS

The present application is National Phase of International Application No. PCT/JP2009/071534 filed Dec. 25, 2009, and claims priorities from, Japanese Applications No. U-2008-009181 filed Dec. 26, 2008; No. U-2008-009182 filed Dec. 26, 2008; No. U-2009-001398 filed Mar. 10, 2009; and No. U-2009-001399 filed Mar. 10, 2009, the disclosure of which are hereby incorporated by reference herein in its entirety.

TECHNICAL FIELD

The present invention relates to a cover for a gas mist pressure bath used for taking a gas mist pressure bath, in which a mist (called as "gas mist" hereafter) is prepared by pulverizing and dissolving carbon dioxide or oxygen, and liquid or a mixed gas (called as "gas" hereafter) of carbon dioxide, oxygen and liquid, and the thus prepared gas mist is directly contacted to a skin and mucous membrane of a human living-body at pressure of not less than a predetermined value.

BACKGROUND ART

It has conventionally been known that carbon dioxide (carbonic acid anhydride: $CO_2$, called as "carbon dioxide" hereafter) has both properties of being not only soluble in water (water-soluble) but also soluble in fat (fat-soluble) and, therefore, by only contacting the skin and mucous membrane of the living-body which is like mixed with water and fat, carbon dioxide penetrates under a subcutaneous layer and expands blood vessels around parts of penetrated carbon dioxide, and it works to improve a blood circulation. Owing to this action of accelerating the blood circulation, it displays various physiological effects such as dropping of blood pressure, improving of metabolism or accelerating to remove pain substance or waste product. Further, it has also anti-inflammation and anti-bacterial. Therefore, carbon dioxide has recently been given attentions also from viewpoints of improving health or beauty other than the purpose of medical cares.

Carbon dioxide in the tissue of the living-body works to release oxygen carried in combination with hemoglobin in a red blood cell. Around parts at a high density of carbon dioxide, the red blood cell releases more oxygen. Thus, supply of oxygen to cells by the red blood cell is mainly controlled by carbon dioxide. In short, being without carbon dioxide, hemoglobin remains as combined with oxygen and the cell becomes unable to receive oxygen. As is seen, carbon dioxide seems to be a waste product resulted from action of the cell, however, it plays in fact very important roles in the human living-body.

Further, in recent times, oxygen of high density has also widely been known as effective in activity of metabolism, accelerating the blood circulation, fatigue recovery, or stability of blood pressure. Other than them, oxygen has disinfection or sterilization by oxidative effect.

Therefore, for causing to directly absorb carbon dioxide or oxygen into a living body, an inventor of this invention has proposed a gas mist pressure bath device and a gas mist pressure bath system using the cover for the gas mist pressure bath.

SUMMARY OF INVENTION

Problems to be Solved by the Invention

However, the conventional cover to be used for the gas mist pressure bath was involved with problems of requesting time for taking off an adhesive part or a fixing part of the cover each time when exhausting air, gas or a gas mist within the cover. Further, also, when pressure within the cover for the gas mist pressure bath became too high, similarly, the adhesive part or the fixing part were once taken off, and the gas mist had to be again fed.

In view of the above circumstances, it is an object of the present invention to provide a cover for the gas mist pressure bath which causes gas of even a small amount to be efficiently absorbed into the skin and mucous membrane of the living body, and which can also easily exhaust air, gas or the gas mist within the cover for the gas mist pressure bath, or adjust pressure within the cover.

Means for Solving the Problem

For solving the above mentioned problems, the present invention is to provide the cover for the gas mist pressure bath (often called, hereafter, as "the gas mist pressure bath cover", or merely "the cover" as the case may be), in which a mist (called as "gas mist" hereafter) is prepared at a density of not less than a predetermined value by pulverizing and dissolving carbon dioxide or oxygen and liquid, or a mixed gas (called as "gas" hereafter) of carbon dioxide, oxygen and liquid, and the thus prepared gas mist is sealed in the cover and is directly contacted to the skin and mucous membrane of the living-body. The cover for the gas mist pressure bath comprises the cover member for covering the skin and mucous membrane of the living-body; an adhesive part provided on a circumferential margin of the living-body cover member for adhering the cover member to the skin and mucous membrane of the living-body;

a gas mist supply port communicating with the cover member for introducing the gas mist into the cover for the gas mist pressure bath; and an outlet for exhausting air, the gas mist or gas sealed in the cover for the gas mist pressure bath and controlling the amounts of them; and is characterized by composing a flat shaped patch enabling to store the gas mist and gas inside thereof by means of the living-body cover member and the adhesive part.

By the way, the invention refers it as "pulverizing and dissolving" to pulverize liquid into fine liquid drops, and cause to contact and mix with gas (carbon dioxide, or oxygen, or mixed gas of carbon dioxide and oxygen).

Herein, the cover for the gas mist pressure bath according to the present invention is desirably further provided with a pressurizing means for pressurizing the inside of the living-body cover member.

The cover for the gas mist pressure bath according to the invention is preferably further provided with a fixing means for fixing the cover to the living-body. This fixing means is desirably made of any one of or plural combination of rubber, string, face fastener or one-touch buckle.

The gas mist supply port has preferably a check valve inside thereof.

The pressurizing means is composed of a hollow gas storage communicating with the living-body cover member, and pressurizes the gas storage to exhaust the gas mist and gas therein into the cover for the gas mist pressure bath in order to carry out pressurization. Between the gas storage and the living-body cover member, there is desirably provided a connection part having a check valve inside thereof.

Otherwise, the pressurizing means is composed of a reducing means of the living-body cover member, so that the reducing means may reduce the cover member at its end to carry out pressurization.

Advantageous Effect of the Invention

Depending upon the present invention, not requiring a much amount of gas, while exhausting air within the cover for the gas mist pressure bath, and easily adjusting pressure in the cover, it is possible to cause the gas mist to be absorbed into the skin and mucous membrane of the living body.

DESCRIPTION OF EMBODIMENTS

In the following description, explanations will be made to embodiments of this invention in detail, referring to the attached drawings.

First Embodiment

Figure 1:
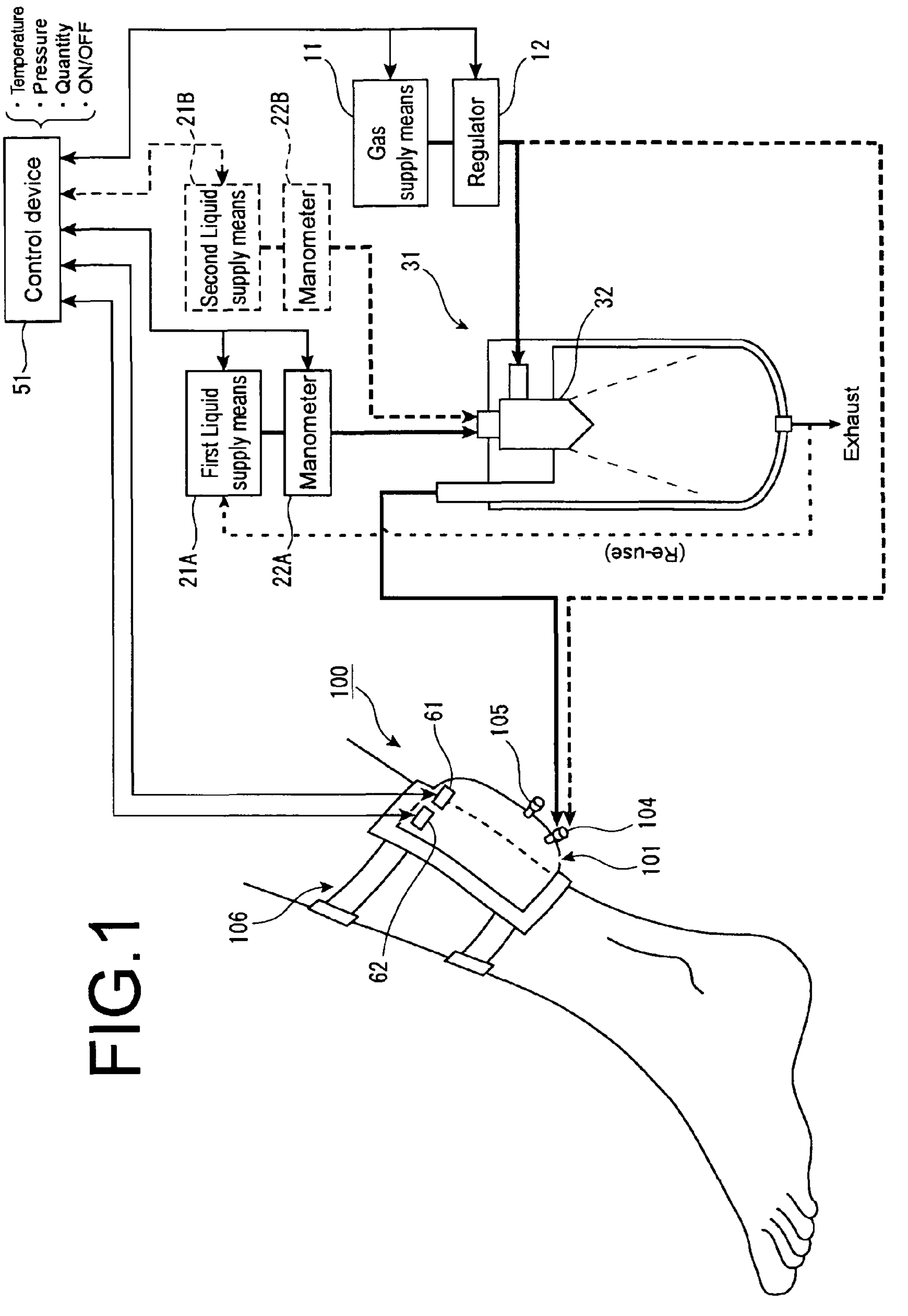
FIG. 1 A typical view showing one example of the gas mist pressure bath system applied with the cover for the gas mist pressure bath depending on a first embodiment of the invention.

The gas mist pressure bath system of this embodiment applying the cover for the gas mist pressure bath of the invention will be referred to. FIG. 1 is the typical view showing one example of the gas mist pressure bath system. As shown in this view, the gas mist pressure bath system of this embodiment comprises a gas supply means 11, a liquid supply means 21, a gas mist supply device 31 generating and supplying the gas mist prepared by pulverizing and dissolving liquid and gas (carbon dioxide or oxygen or the mixed gas of carbon dioxide and oxygen), the cover 100 for the gas mist pressure bath forming a space of sealing inside the supplied gas mist, and a control device 51 generating and controlling to supply the gas mist.

The gas mist supply means 11 supplies gas to the gas mist supply means 31, provided that if the mist is enough supplied in the cover 100 for the gas mist pressure bath, only gas is directly supplied from the gas mist supply means 11 into the cover 100. It is optimum to use a gas bomb as the gas mist supply means 11. The gas mist supply means 11 is provided with a regulator 12 for controlling gas pressure. Omitting to show, the gas supply means 11 may be disposed with a heater for heating gas or a thermometer for controlling temperatures.

The liquid supply means 21 is composed of a pump or the like and supplies liquid to the gas mist supply device 31. As the liquid, it is suitable to use water, ionic water, physiological salt solution, ozone water, purified water or sterilized water. Further, these liquids may contain medicines useful to user's diseases or symptoms. For the medicines, enumerated are, for example, anti-allergic agent, anti-inflammatory agent, anti-febrile, anti-fungus agent, anti-influenza virus, carcinostatic substance, anti-hyper tensive agent, cosmetic agent, or trichogen. Further, these liquids are further possible to generate synergistic effects by coupling with a gas physiological action with single or plurality of menthol having a cooling action; vitamin E accelerating circulation of the blood; vitamin C derivative easily to be absorbed to a skin tissue and having a skin beautifying effect; retinol normalizing a skin keratinizing action and protecting the mucous membrane; anesthetic moderating irritation to the mucous membrane; cyclodextrin removing odor; photocatalysis or a complex of photocatalysis and apatite having disinfection and anti-phlogiston; hyaluronic acid having excellent water holding capacity and a skin moisture retention effect; coenzyme Q10 activating cells and heightening immunization; a seed oil containing anti-oxidation and much nutrient; or propolith having anti-oxidation, anti-fungus, anti-inflammatory agent, pain-killing, anesthetic, and immunity. Otherwise, the liquids may be added with ethanol, gluconic acid chlorohexizine, ampholytic surface active agent, benzalkonium chloride, alkyldiamino ether glycin acetate, sodium hypochlorite, acetyl hydroperoxide, sodium sesquicarbonate, silica, povidoneiodine, sodium hydrogen carbonate. In addition, high density carbonate spring may be added (as examples organic components, sulfate, carbonate, sodium dichloroisocyanurate).

Further, as shown in FIG. 1, plural liquid supply means 21A, 21B may be arranged for respectively different liquids. The liquid supply means 21 is furnished with pressure gauges 22 (22A, 22B) respectively for controlling supply pressure. In addition, it is desirable to dispose a heater (not shown) heating the liquid (for example, heating to a hot water of around 40° C.) or a thermometer (not shown).

The gas mist supply means 31 is a device for supplying under pressure the gas mist into the living-body pressure bath cover 100, the gas mist being prepared by pulverizing and dissolving the liquid from the liquid supply means 21 and gas from the gas supply means 11. Gas is accelerated in absorption into the skin and mucous membrane by supplying under a condition of the gas mist of pulverizing and dissolving together with liquid. Size of the mist is optimum to be not larger than 10 μm. Herein, there is shown an example of the gas mist generated by using high speed flow of gas supplied from the gas supply means 11 by the fluid nozzle 32 and this gas mist fed to the gas mist pressure bath cover 100. Other than this, there may be used gas mist supply devices of various systems such as jetting gas at high pressure into liquid to generate the gas mist, or of utilizing super sonic wave to generate the same.

The control device 51 is composed of a computer having CPU, memory and display. This performs under an optimum condition various kinds of controls such as pressure control or on-off switch of gas supplied from the gas supply means 11; gas supply to the gas mist supply means 31/the cover 100 for the gas mist pressure bath; supply pressure control and temperature control of liquid from the liquid supply means 21; and on-off switch of supply from the gas mist supply means 31. In particular, it is preferable to compose a structure as stopping of supplying gas from the gas supply means 11 by the control device 51, when the pressure value within the cover 100 becomes more than a predetermined value.

Figure 2:
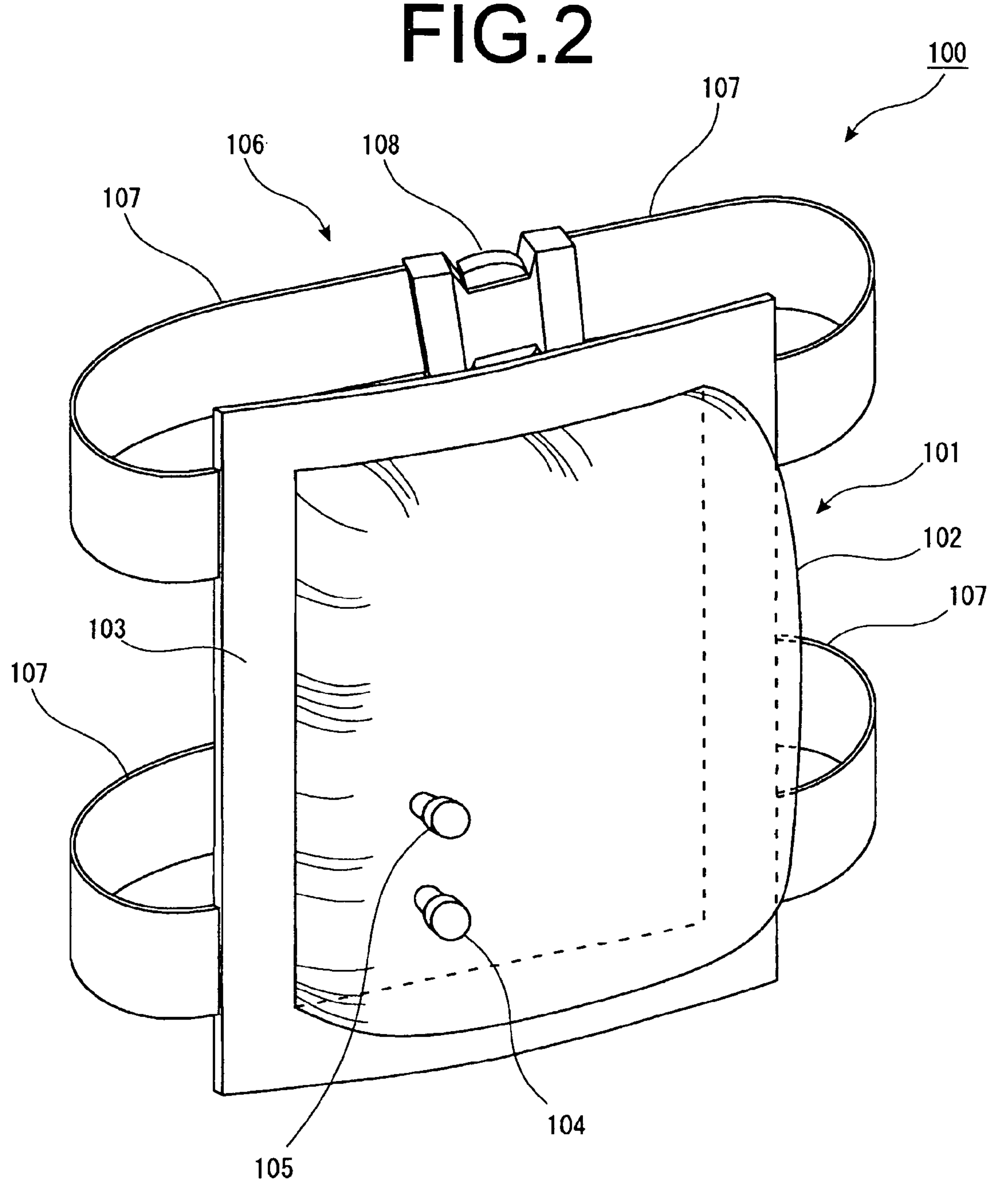
FIG. 2 A generally schematic view of the cover for the gas mist pressure bath depending on the first embodiment of the invention.
Figure 3:
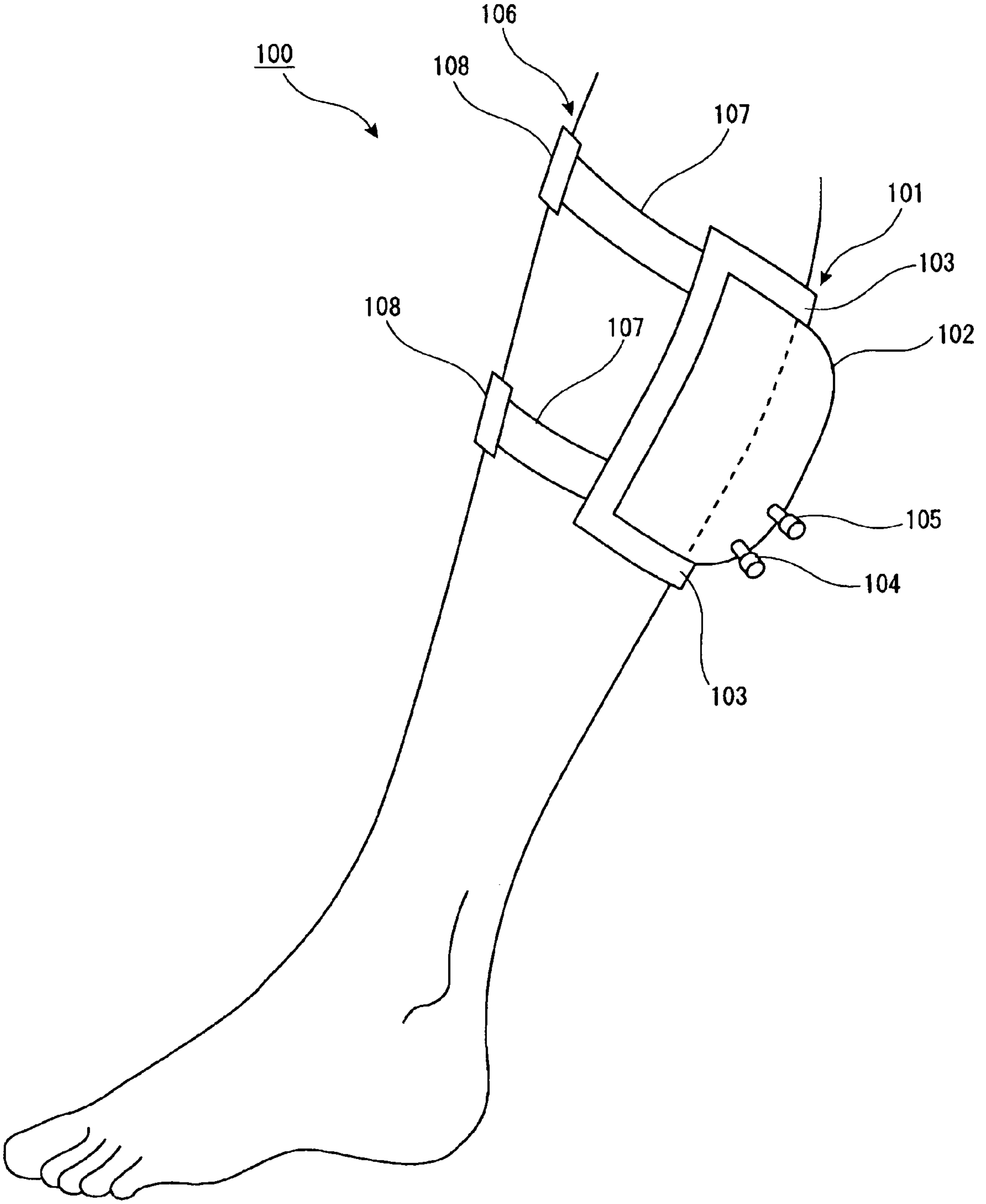
FIG. 3 A typical view showing an attaching condition of the cover for the gas mist pressure bath depending on the first embodiment of the invention.
Figure 4:
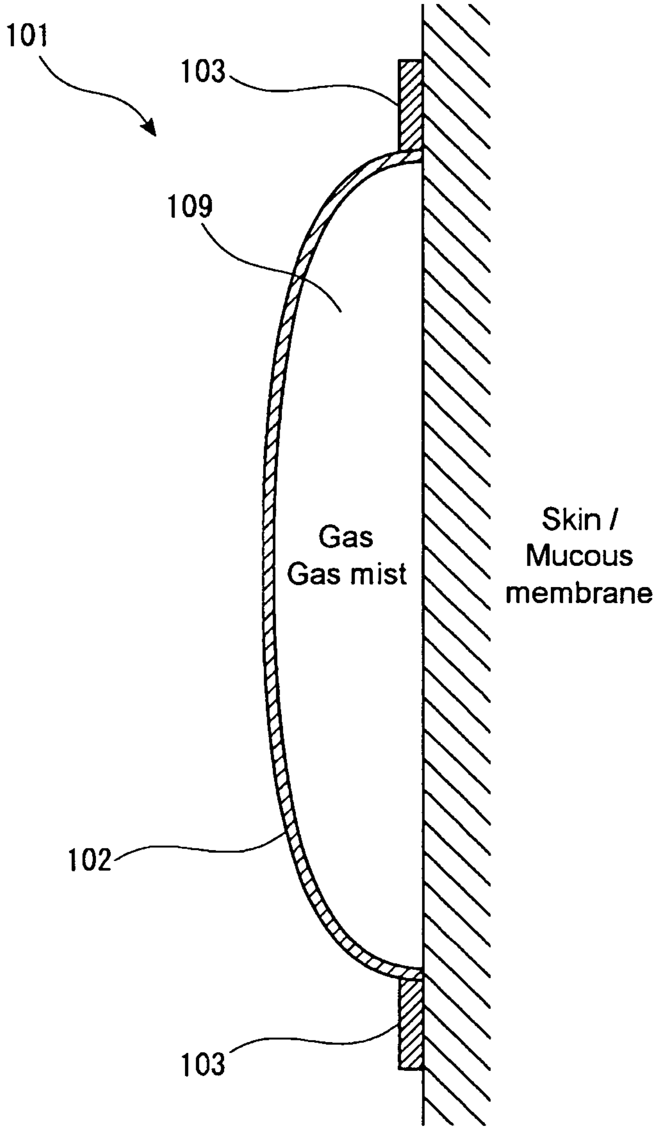
FIG. 4 A vertically cross sectional and typical view in the cover main body for the gas mist pressure bath depending on the first embodiment of the invention.

The cover 100 for the gas mist pressure bath is a patch-shaped cover forming a space for sealing the gas mist and gas inside thereof, and can cover the skin and mucous membrane of the living body (herein, as the examples, the living body's lower extremity). FIG. 2 is the generally schematic view of the cover for the gas mist pressure bath depending on the first embodiment of the invention, and FIG. 3 is the typical view Showing the attaching condition of the cover for the gas mist pressure bath. FIG. 4 is the vertically cross sectional and typical view in the cover main body for the gas mist pressure bath.

The cover 100 is, as shown in them, composed of the cover main body 101 for the pressure bath and the fixing part 106 for fixing the cover main body 101 to the living-body. The cover main body 101 is composed of the living-body cover member 102 composing the flat-shaped patch for covering the skin and mucous membrane of the living-body (herein, as the examples, the living body's lower extremity); the adhesive part 103 provided on the circumferential margin of the living-body cover member 102 for adhering the cover member to the skin and mucous membrane of the living-body; the supply port 104 provided at the cover member 102 for introducing the gas mist and gas into the living-body cover member 102; and an outlet 105 for controlling the amounts of air, gas mist and gas within the living-body cover member 102 and exhausting them. The fixing part 106 is composed of a stopping belt 107 and a belt stopper 108.

The living-body cover member 102 covers the skin and mucous membrane of the living-body and, as shown in FIG. 4, enables to form the space 109 for storing the gas mist and gas between the cover main body 101 and the skin and mucous membrane. The living-body cover member 102 is made of the woven or non-woven fabric of a pressure resistant, non-air permeable and non-moisture permeable materials, for example, preferably, the natural rubber, silicone rubber, polyethylene, polypropylene, polyvinylidene, polystylene, polyvinylacetate, polyvinyl chloride, polyamide resin, polytetrafluoroethylene.

The living-body cover member 102 has an adhesive part 103 on its perimeter the adhesive part 103 for avoiding leakage of the gas mist and gas within the cover main body 101. At the side of the adhesive part 103 to the skin and mucous membrane, there is disposed a material adhering the living-body's skin and mucous membrane. The adhesive material is preferably a viscoelastic gel of polyurethane or silicone rubber, and such a part is optimum which is exchangeable each time when viscosity becomes weak.

The gas mist supply port 104 communicates with the space 109 of the living-body cover member 101 for leading the gas mist and gas into the inside of the living-body cover member 101. The gas mist and gas are supplied into the inside of the living-body cover member 101 by connecting the supply means such as the gas mist supply means 31 and the gas supply means 11 to the gas mist supply port 104. The check valve is provided inside of the gas mist supply port 203 for checking flow-back of the gas mist and gas.

The outlet 105 is an air hole of exhausting air, the gas mist and gas when taking out air from the pressure bath cover main body 101 or when controlling pressure by drawing out gas or the gas mist therein. The outlet 105 has such a structure usually stopping air flow with a valve or cap, and allowing it by getting out the valve or cap only when taking out air. The pressure control may be carried out manually, but desirably automatically by a control device 51 together with supply control of gas and the gas mist based on measuring values of a manometer 61. Otherwise, a safety valve (recess valve) may be provided as the outlet 105 for automatically opening a valve when the inside of the living-body pressure bath cover 101 becomes more than a constant pressure.

The fixing part 106 is made, herein as an example, of a stopping belt 107 and a belt stopper 108. As to the stopping belt 107, for meeting users' various body figures or their using parts, the stopping belt 107 is desirably composed of a material having stretching property as a rubber. The view shows an example of arranging four pieces of stopping belts 107 and securing at upper and lower two portions, and the arranging number and positions may be changed in view of the shapes of the cover main body 101 or the users' using parts. The belt stopper 108 is preferably one-touch buckle of easily attaching and detaching the stopping belt 107. Further, an adjuster may be provided for easily adjusting a length of the stopping belt 107.

The pressure bath cover member 101 is inside installed with a manometer 61 for measuring an inside pressure. The control device 51 controls supply of the gas mist and gas on the basis of measuring values of the manometer 61 for maintaining a pressure value within the gas mist pressure bath cover 101 to be more than 1 air pressure (more preferably, around 1.02 to 2.5 air pressure). Further, the pressure bath cover main body 101 is inside installed with a thermometer 62 for measuring an inside temperature in the pressure bath cover main body 101. The control device 51 performs on-off of a heater installed in the liquid supply means 21 on the basis of measuring values of the thermometer 62 for maintaining a predetermined temperature (for example, around 38° C.) bringing about warm bath effects within the pressure bath cover main body 101.

Now, explanation will be made to the above mentioned gas mist pressure bath system and a method of performing the gas mist pressure bath using the gas mist pressure bath cover 100 of this invention. At first, the pressure bath cover main body 101 is adhered by the adhesive part 103 to a living-body's part requesting the gas mist pressure bath (herein, the living-body's lower extremity), and is made an almost sealed condition in the cover member 101. Next, the stopping belt 107 is stopped by the belt stopper 108 to secure the cover member 101 to the living-body. Air is in advance exhausted as much as possible from the outlet 105. Gas is supplied from the gas supply means 11 to the gas mist supply means 31, while liquid is supplied from the liquid supply means 21 to the same. At this time, the control device 51 controls the liquid and gas supplying pressure, amount and temperature. Thereby, the gas mist supply means 31 generates the gas mist, and the generated gas mist is supplied from the supply port 104 to the inside of the living-body cover member 101. When the mist is enough supplied in the cover member 101, only gas is supplied into the cover 101 from the gas mist supply means 11. The control device 51 is controlled such that the inside of the pressure bath cover 101 becomes an optimum pressurized and heated condition (around 1.02 to 2.5 air pressure and around 38° C.) in view of the measuring values of the manometer 61 and the thermometer 62, and when pressure becomes too high, or when the gas mist and air are exchanged, it is possible to easily exhaust air from the outlet 105. Under such conditions, the optimum gas mist pressure bath is carried out.

Figure 5:
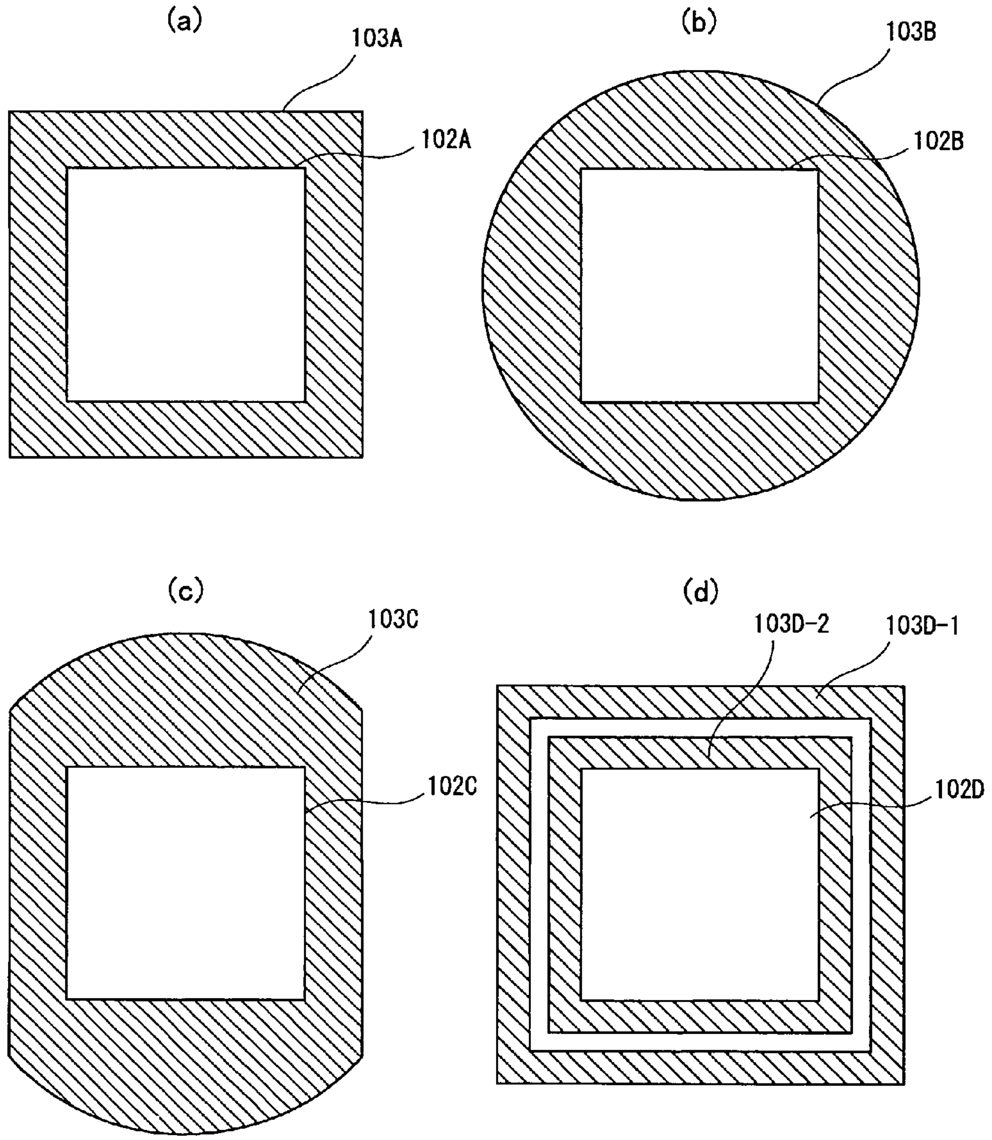
FIG. 5 Typical views showing examples of shapes of the adhesive parts in the covers of the gas mist pressure bath depending on the invention.

The above embodiment illustrates a rectangular pressure bath cover main body 101, but various shapes may be employed according to the parts of the living-body to be attached. FIG. 5 shows one example of the shape of the adhesive part 103. As shown in FIG. 5(*a*), the cover member 102A and the adhesive part 103A may be almost similar in the circumferential shape, and as shown in FIG. 5(*b*) and (*c*), the shapes of the perimeters of the living-body cover members 102B and 102C may be quite different from those of the adhesive parts 103B and 103C. Further, as seeing in FIG. 5(*d*), encircling the living-body cover member 102D, a plurality of (herein, as the example, two) adhesive parts 103D-1, 103D-2 may be provided.

Figure 6:
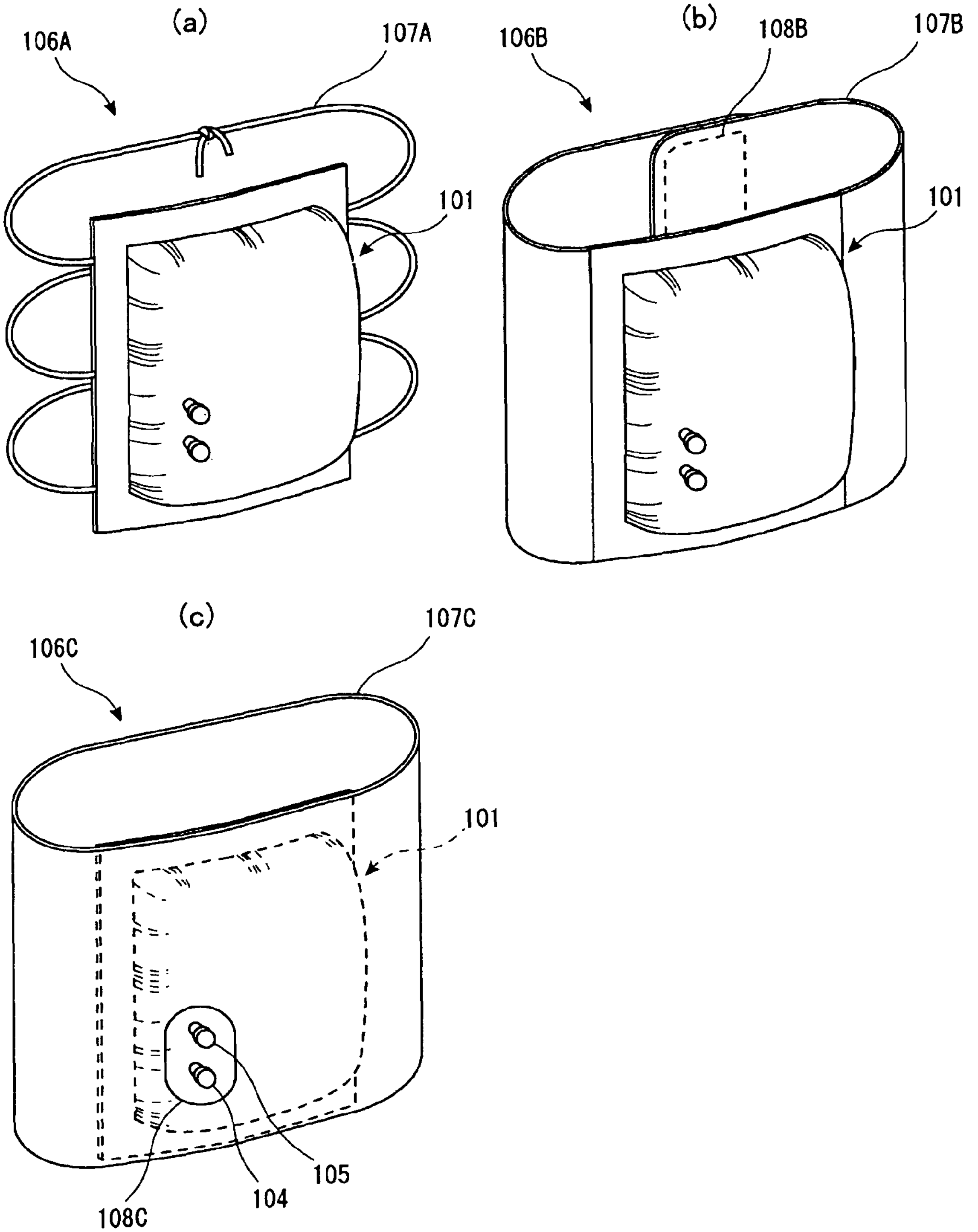
FIG. 6 Typical views showing examples of shapes of the adhesive parts in the fixing means of the covers for the gas mist pressure bath depending on the invention.

In addition, in the above embodiment, the fixing part 106 of the pressure bath cover main body 101 is composed of the stopping belt 107 and the belt stopper 108, but other than this, many shapes may be employed. FIG. 6 shows examples of the fixing part 106. FIG. 6(*a*) shows an example where the strings 107A are provided and knotted at good parts to secure the cover main body 101, FIG. 6(*b*) shows another example where the rubber belt 107B and the face fastener 108B are provided and adhered to the good part to secure the cover main body 101, and FIG. 6(*c*) shows a further example where the cover main body 101 and the fixing part 106 are not made one-body. Herein, a supporter 107C with elasticity having an opening 108C exposing at least the gas mist supply port 104 and an outlet 105.

The above mentioned embodiments have shown the examples of applying the cover for the gas mist pressure bath to the human living-body, but the invention may be applied not only to the human living body but to animals.

Second Embodiment

Figure 7:
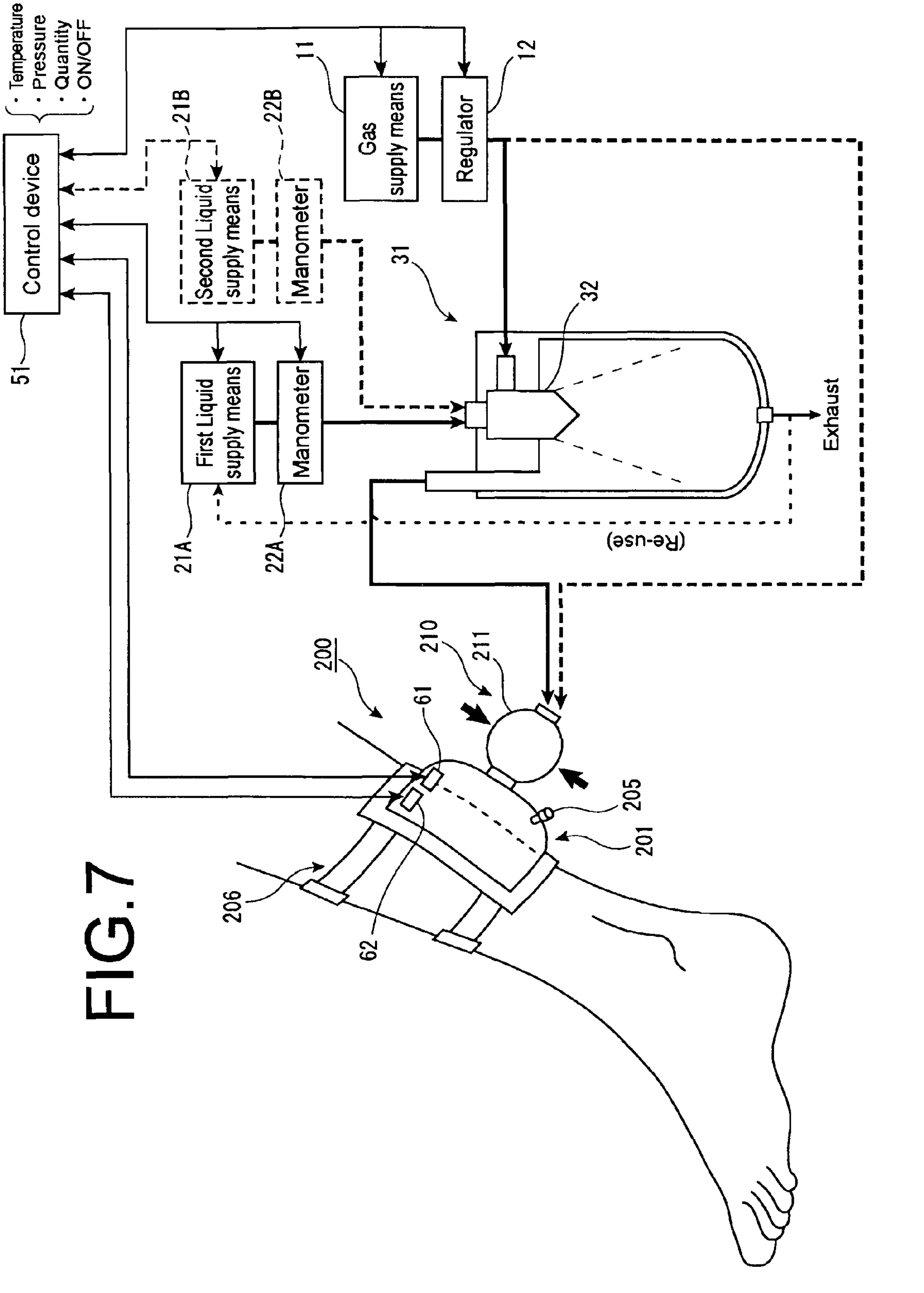
FIG. 7 A typical view showing one example of the gas mist pressure bath system applied with a second embodiment of the invention.

FIG. 7 is the typical view showing one example of the gas mist pressure bath system applied with the cover for the gas mist pressure bath depending on the second embodiment of this invention. This embodiment will explain the cover for the gas mist pressure bath further having a pressurizing means for easily pressurizing the inside of the living-body cover. As to the same parts as those of the first embodiment shown in FIG. 1, the same numerals will be given, and detailed explanation will be omitted.

As shown in FIG. 7, other than the living-body cover member 201 of covering the skin and mucous membrane of the living body and forming the space for sealing inside the gas mist and gas, the cover 200 for the gas mist pressure bath of this embodiment has the pressurizing part 210 for pressurizing the inside of the living-body cover member 201.

Figure 8:
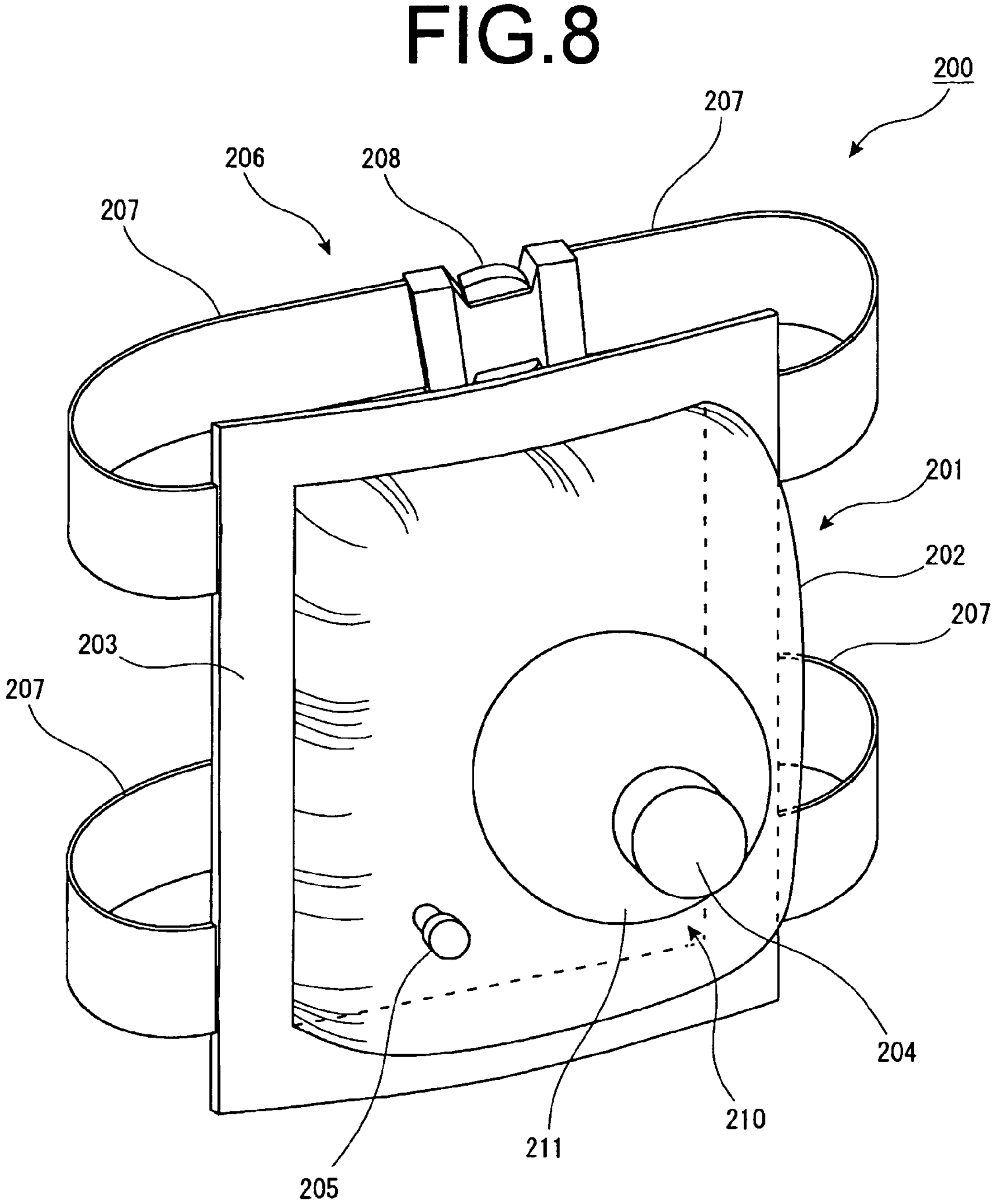
FIG. 8 A generally schematic view of the cover for the gas mist pressure bath depending on the second embodiment of the invention.
Figure 9:
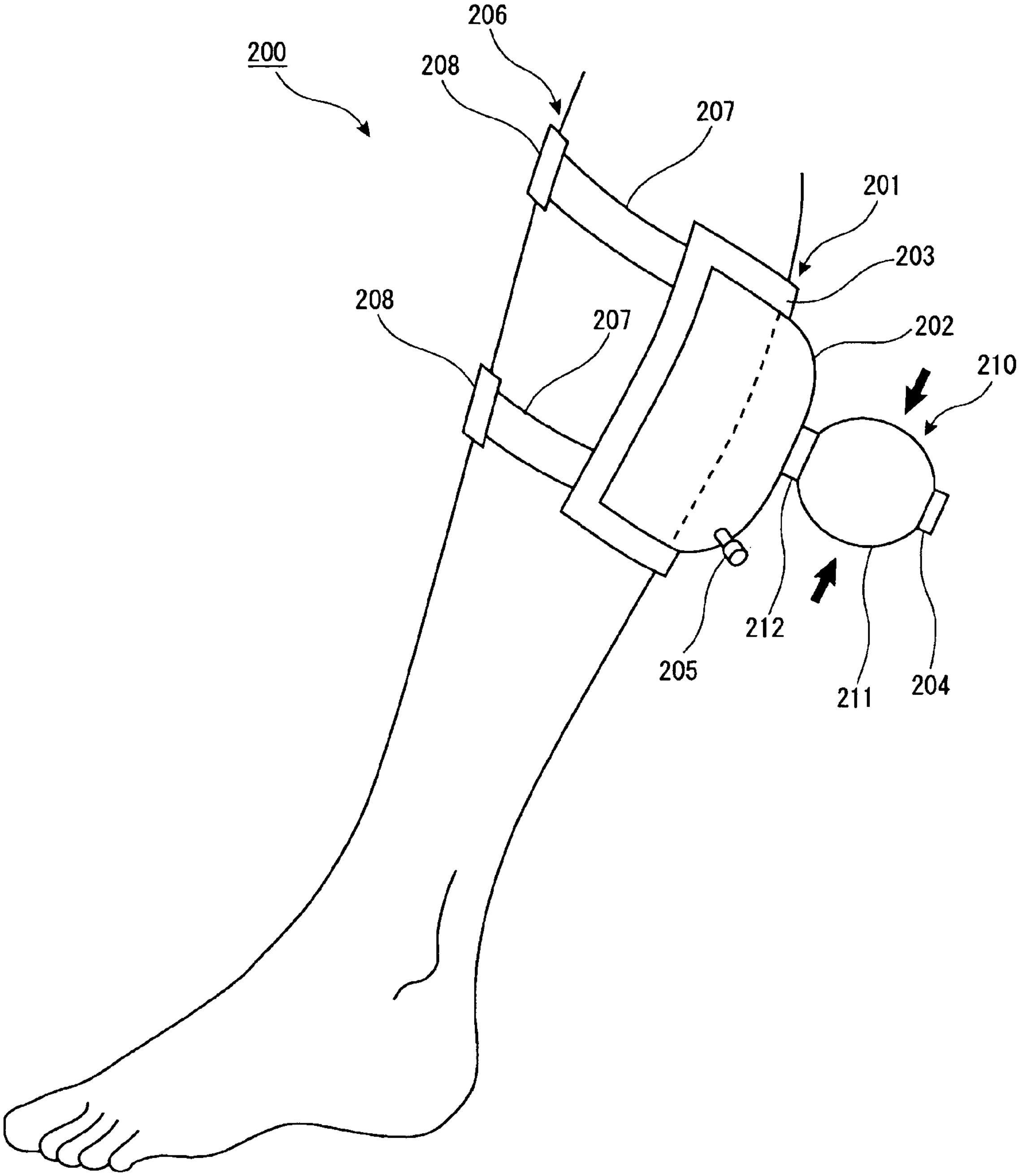
FIG. 9 A typical view showing an attaching condition of the cover for the gas mist pressure bath depending on the second embodiment of the invention.

In the following, explanation will be more concretely made to the gas mist pressure bath cover 200 based on FIGS. 8 to 10. FIG. 8 is the generally schematic view of the cover for the gas mist pressure bath depending on the second embodiment of the invention, FIG. 9 is the typical view showing the attaching condition, and FIG. 10 is the vertically cross sectional and typical view in the cover main body depending on the second embodiment of the invention.

As shown in these Figures, the cover 200 for gas mist pressure bath is composed of a cover main body 201 for the pressure bath, a fixing part 206 for fixing the cover main body 201 to the living-body, and a pressurizing part 210 for pressurizing the inside of the cover main body 201. The cover main body 201 is composed of a living-body cover member 202 composing a flat-shaped patch for covering the skin and mucous membrane of the living-body (herein, as the example, the living body's lower extremity); an adhesive part 203 provided on the circumferential margin of the living-body cover member 202 for adhering the cover member to the skin and mucous membrane of the living-body; a supply port 204 having a check valve 204*a* inside thereof, provided at the cover member 202 for introducing the gas mist and gas into the pressure bath cover member 201 via the pressurizing part 210; and an outlet 205 for controlling the amounts of air, gas mist and gas within the living-body cover member 201 and exhausting them. Further, the part 206 is composed of the pressurizing part 210, a hollow gas storage 211 having a check valve 212*a* inside thereof and a connection part 212 for connecting the gas storage 211 and the living-body cover member 202.

Figure 10:
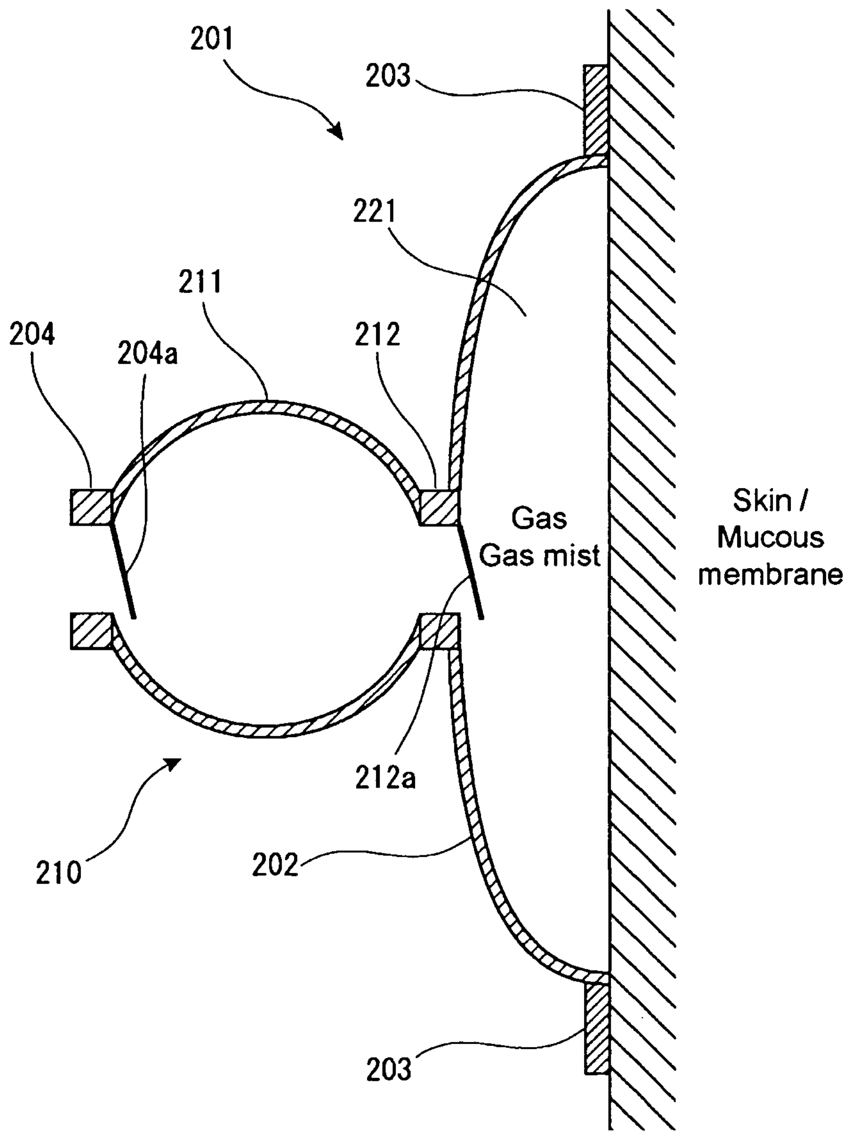
FIG. 10 A vertically cross sectional and typical view in the cover main body for the gas mist pressure bath depending on the second embodiment of the invention.

The living-body cover member 202 covers the skin and mucous membrane of the living-body and, as shown in FIG. 10, enables to form the space 221 for storing the gas mist and gas between the cover main body 201 and the skin and mucous membrane. The living-body cover member 202 is made of the woven or non-woven fabric of a pressure resistant, non-air permeable and non-moisture permeable materials, for example, preferably, the natural rubber, silicone rubber, polyethylene, polypropylene, polyvinylidene, polystyrene, polyvinyl acetate, polyvinyl chloride, polyamide resin, polytetrafluoroethylene.

The living-body cover member 202 has the adhesive part 203 on its perimeter the adhesive part 103 for avoiding leakage of the gas mist and gas within the cover main body 201. At the side of the adhesive part 203 to the skin and mucous membrane, there is disposed a material adhering the living-body's skin and mucous membrane. The adhesive material is preferably a viscoelastic gel of polyurethane or silicone rubber, and such a part is optimum which is exchangeable each time when viscosity becomes weak.

The gas mist supply port 204 communicates with the inside of the living-body cover member 210 via the pressurizing part 210 for leading the gas mist and gas into the inside of the living-body cover member 201. The gas mist supply port 204 is connected with a supply means of the gas mist and gas of the gas mist supply means 31 and the gas supply means 11 for leading the gas mist and gas into the inside of the living-body cover member 201. The check valve 204*a* is provided inside of the gas mist supply port 204 for checking flow-back of the gas mist and gas. By the way, in the gas mist pressure bath cover 200 shown in FIGS. 7 to 10, the gas mist and gas from the gas mist supply means 31 and the gas supply means 11 are at first supplied from the supply port 204 to the pressurizing part 210, and supplied into the living-body cover member 202 via the connection part 212.

The outlet 205 is an air hole of exhausting air, the gas mist and gas when taking out air from the gas mist pressure bath cover 201 or when adjusting pressure by drawing out gas or the gas mist therein. The outlet 205 has such a structure stopping usually air flow by a valve or cap, and allowing it by getting out the valve or cap only when taking out air. The pressure control may be carried out manually, but desirably automatically by a control device 51 together with supply control of gas and the gas mist based on measuring values of a manometer 61. A safety valve (recess valve) may be provided as the outlet 204 for automatically opening a valve when the inside of the pressure bath cover main body 201 becomes more than constant pressure.

The pressurizing part 210 is a means for pressurizing the inside of the living-body cover member 202, and is herein composed of the hollow air storage 211 communicating with the living-body cover member 202 and the connection part 212 connecting the air storage 211 and the living-body cover member 202. The pressurizing part 210 introduces the gas mist and gas into the living-body cover member 202, and at the same time also stores the gas mist and gas also in the gas storage 211, and if pressurizing as crushing the gas storage 211 as showing with arrows in FIG. 9, the gas mist or gas in the gas storage 211 is exhausted into the living-body cover member 202 via the connection part 212. Thereby, the inside of the living body cover member 202 can be pressurized.

The pressurizing part 210 may be structured as pressurizing manually, and mechanically by controlling the control means 51 using a driving device. Pressurization in the gas mist pressure bath heightens effects by performing an interval pressurization in pulse, and so the pressurizing part 210 may be pressed intermittently at constant rhythm. The pressurizing interval heightens effects by synchronizing with pulsation of pulse.

The fixing part 206 is made, herein as an example, of a stopping belt 207 and a belt stopper 208. As to the stopping belt 207, for meeting users' various body figures or their using parts, the stopping belt 207 is desirably composed of the material having stretching property as a rubber. The view shows an example of arranging four pieces of stopping belts 207 and securing at upper and lower two portions, and the arranging number and positions may be changed in view of the shapes of the cover main body 101 or the users' using parts. The belt stopper 208 is preferably one-touch buckle of easily attaching and detaching the stopping belt 207. Further, an adjuster may be provided for easily adjusting a length of the stopping belt 207.

The pressure bath cover member 201 is inside installed with a manometer 61 for measuring inside pressure. The control device 51 controls supply of the gas mist and gas on the basis of measuring values of the manometer 61 for maintaining a pressure value within the gas mist pressure bath cover 101 to be more than 1 air pressure (more preferably, around 1.02 to 2.5 air pressure). Further, the pressure bath cover main body 201 is inside installed with a thermometer 62 for measuring inside temperatures in the pressure bath cover main body 201. The control device 51 performs on-off of a heater installed in the liquid supply means 21 on the basis of measuring values of the thermometer 62 for maintaining a predetermined temperature (for example, around 38° C.) bringing about warm bath effects within the pressure bath cover main body 101.

Now, explanation will be made to the above mentioned gas mist pressure bath system and a method of performing the gas mist pressure bath using the gas mist pressure bath cover 201 of this invention. At first, the pressure bath cover main body 201 is adhered by the adhesive part 203 to a living-body's part requesting the gas mist pressure bath (herein, the living-body's lower extremity), and is made an almost sealed condition in the cover member 201. Next, the stopping belt 207 is stopped by the belt stopper 208 to secure the cover member 201 to the living-body. Air is in advance exhausted as much as possible from the outlet 205. Gas is supplied from the gas supply means 11 to the gas mist supply means 31, while liquid is supplied from the liquid supply means 21 to the same. At this time, the control device 51 controls the liquid and gas supplying pressure, amounts and temperatures. Thereby, the gas mist supply means 31 generates the gas mist, and the generated gas mist is supplied from the supply port 204 to the inside of the living-body cover member 202 via the gas storage 211 and the connection part 212. When the mist is enough supplied in the cover member main body 201, only gas is supplied into the cover 201 from the gas mist supply means 11. The control device 51 is controlled such that the inside of the pressure bath cover 201 becomes an optimum pressurized and heated conditions (around 38° C.) in view of the measuring value of the thermometer 62. When the gas mist and gas are stored at the appropriate amounts in the cover main body 201 and the gas storage 211, the control device once stops the supply of the gas mist or gas. Subsequently, the gas storage 211 is pressurized as crushing. Thereby, the gas mist or gas in the gas storage 211 is exhausted into the cover main body 201, and the inside of the cover main body 201 is moderately pressurized (around 1.02 to 2.5 air pressure). When pressure becomes too high, or when the gas mist or gas are exchanged, it is possible to easily exhaust air from the outlet 105. Under such conditions, the optimum gas mist pressure bath is carried out.

In the above embodiment, the pressurizing part is composed of the hollow air storage communicating with the living-body cover member via the connection part, but as far as enabling to easily pressurize the inside of the living-body cover member, any members are sufficient. In the following, other composing examples of the pressurizing part will be explained.

Figure 11:
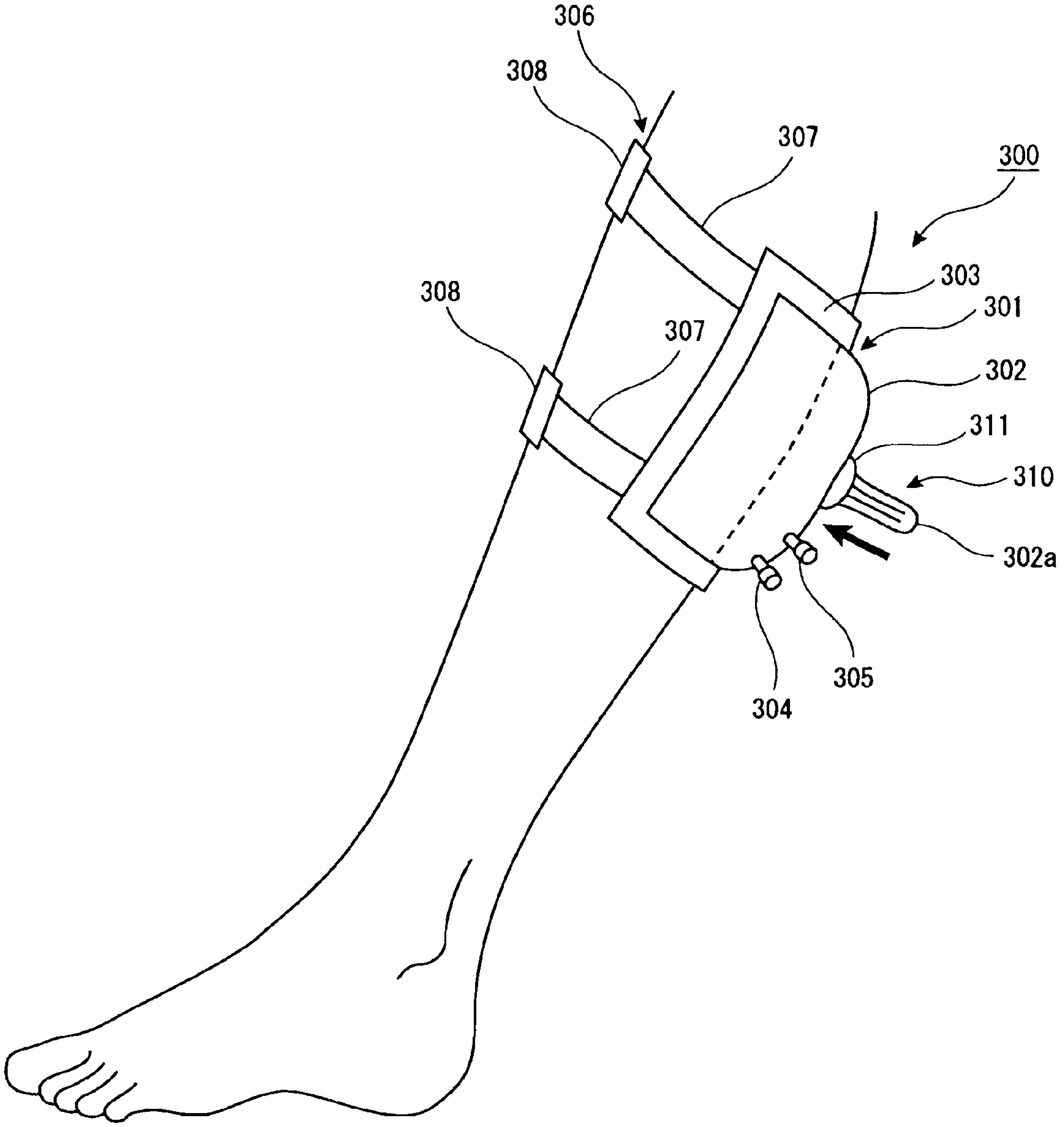
FIG. 11 A typical view (No. 1) showing the other attaching condition of the cover for the gas mist pressure bath depending on the second embodiment of the invention.

FIG. 11 is the typical view (No. 1) showing an example of another pressurizing part for pressurizing the cover for the gas mist pressure bath depending on the second embodiment of the invention. Herein, reference will be made to the living-body cover member cover 300 where the pressurizing part 310 is composed of the reducing ring 311 reducing the living-body cover member 302. In the following, other than that the living-body cover member 302, the supply port 304 and the pressurizing part 310 are different in the structure, since there are the same structures as those of FIG. 9, detailed explanations for respective parts other than the above mentioned will be omitted.

The gas mist pressure bath cover 300 is composed of the pressure bath Cover main body 301, the fixing part 306 for fixing the cover main body 301 to the living-body, and the pressurizing part 306 for pressurizing the inside of the living-body cover member 301.

The pressure bath cover main body 301 is composed of a living-body cover member 302 composing a flat-shaped patch for covering the skin and mucous membrane of the living-body (herein, as the example, the living body's lower extremity); an adhesive part 303 provided on the circumferential margin of the living-body cover member 302 for adhering the cover member to the skin and mucous membrane of the living-body; a supply port 304 having a check valve **304*a* inside thereof, provided at the cover main body 302 for introducing the gas mist and gas into the pressure bath cover main body 301; and an outlet 305 for controlling the amounts of air, gas mist and gas within the living-body cover member 201 and exhausting them. The fixing part 306 is composed of a stopping belt 307 and a belt stopper 308**.

The pressurizing part 310 is composed of the reducing ring 311 formed with an elastic member as a rubber and having a small hole. The reducing ring 311 is passed into its small hole with a front end portion (central part) **302*a* of the living-body cover member 302**, and if sliding in an arrow direction of FIG.

11, the vicinity of the front end portion (central part) 301*a* is reduced by the small hole of the reducing ring 307, so that the space of storing the gas mist and gas of the living-body cover member 301 is made narrow and the inside of the living-body cover member 301 is pressurized.

Herein, as the pressurizing part 310, a clip may be used instead of the reducing ring 310. In short, any means may be sufficient, as far as being possible to reduce the living-body cover member 302 at the front end portion 302*a* so that the space of storing the gas mist and gas of the living-body cover member 301 is made narrow and the inside of the living-body cover member 301 is pressurized.

The pressurizing part 310 (reducing ring 311) may be structured manually slid and fixed, or mechanically by controlling the control device 51. Pressurization by sliding the pressurizing part 310 (reducing ring 311) may be performed by specific interval in pulse. Further on, illustration has been made, taking up the examples of the living body's hand parts, but it is of course to apply to other various parts of the living body.

Figure 12:
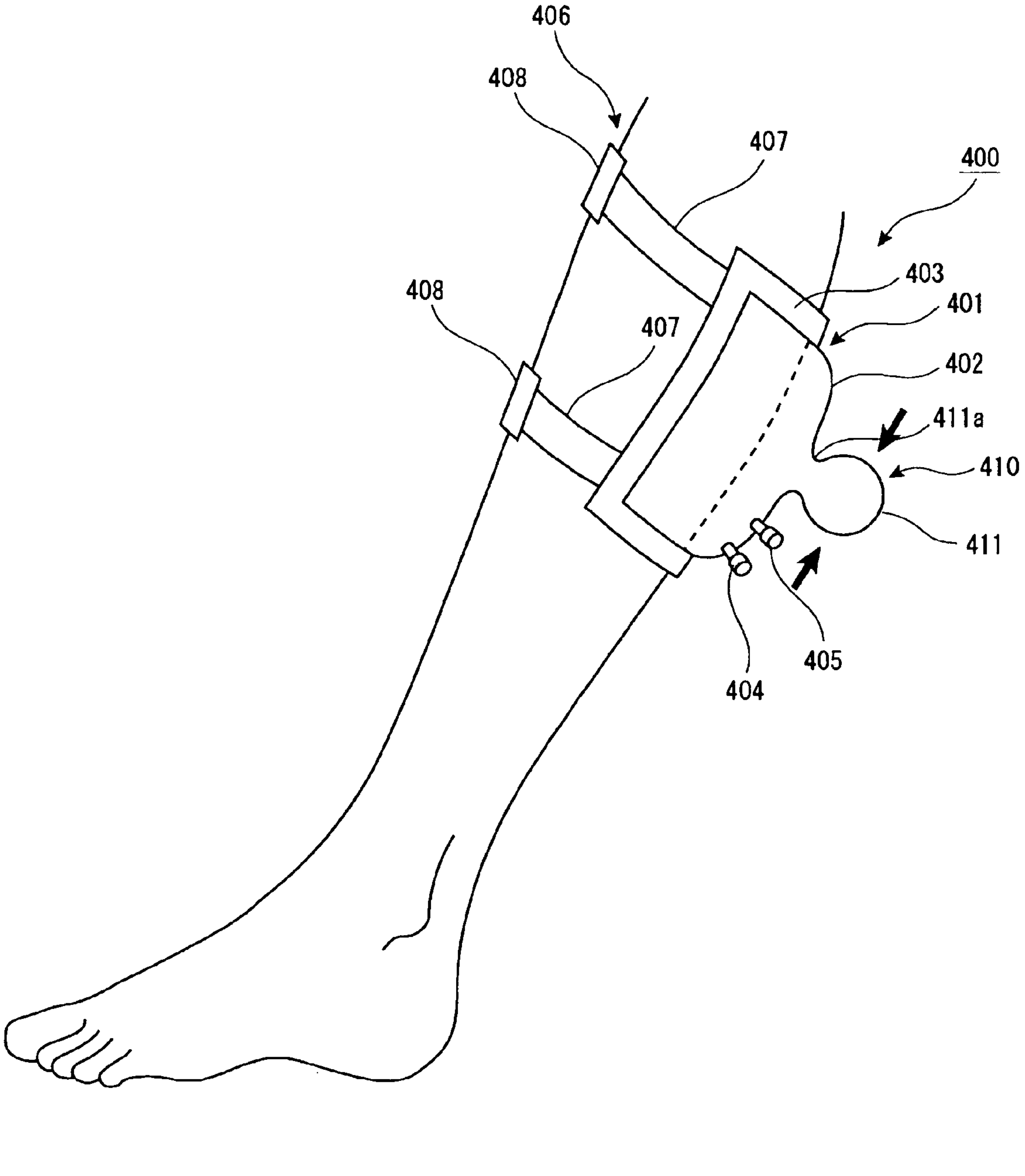
FIG. 12 A typical view (No. 2) showing an attaching condition of the cover for the gas mist pressure bath depending on the second embodiment of the invention.

Next reference will be made to the cover 400 for the gas mist pressure bath where the pressurizing part 410 is composed of an almost spherical hollow gas storage 411. FIG. 12 is the typical view (No. 2) showing another pressurizing part of the cover for the gas mist pressure bath depending on the second embodiment of the invention. In the following, other than that the living-body cover member 402, the supply port 404 and the pressurizing part 410 are different in the structure, since there are the same compositions as those of FIG. 9, detailed explanations for respective parts other than the above mentioned will be omitted.

The gas mist pressure bath cover 400 is composed of the pressure bath cover main body 401, the fixing part 406 for fixing the cover main body 401 to the living-body, and the pressurizing part 410 for pressurizing the inside of the living-body cover member 401.

The pressure bath cover main body 401 is composed of a living-body cover member 402 composing a flat-shaped patch for covering the skin and mucous membrane of the living-body (herein, as the example, the living body's lower extremity); an adhesive part 403 provided on the circumferential margin of the living-body cover member 402 for adhering the cover member to the skin and mucous membrane of the living-body; a supply port 404 having a check valve inside thereof, provided at the cover main body 401 for introducing the gas mist and gas into the pressure bath cover main body 401; and an outlet 405 for controlling the amounts of air, gas mist and gas within the living-body cover member 401 and exhausting them. The fixing part 406 is composed of a stopping belt 407 and a belt stopper 408.

The pressurizing part 410 is composed of an almost spherical gas storage 411 provided in communication with the living-body cover member 402. As shown in FIG. 12, the pressurizing part 410 is sectioned in shape by the cover member 402. By pressurizing as crushing the gas storage 411, the gas mist or gas is exhausted into the pressure bath cover main body 401, so that the inside thereof may be moderately pressurized.

The gas storage 411 may be furnished with an exclusively used cover for covering the whole of the air storage 411. The gas storage 411 may be structured as pressurizing manually, or mechanically by the control means 51. Pressurization by the pressurizing part 410 may be performed by specific interval in pulse. Further on, illustration has been made, taking up the examples of the living body's lower extremity, but it is of course to apply to other various parts of the living body.

Each of the above mentioned embodiments has shown the example of applying the cover for the gas mist pressure bath to the human living-body, but the invention may be applied not only to the human living body but to animals.

With the structure as mentioned above, according to the present invention, it is possible to cause the gas mist to be efficiently absorbed into the skin and mucous membrane of the living body, while easily carrying about exhaust of air in the gas mist pressure bath cover and control of pressure in the cover.

The above explanation has been made to the embodiments of the invention, but the invention is not limited to such embodiments, and so far as not deviating from the subject matter of the invention, various kinds of embodiments are, of course, available.

INDUSTRIAL APPLICABILITY

Thus, the present invention relates to the cover for the gas mist pressure bath, in which the gas mist is prepared by pulverizing and dissolving carbon dioxide or oxygen and liquid, or a mixed gas of carbon dioxide and oxygen and liquid, and is caused to contact the skin and mucous membrane of the living-body at pressure of not less than a predetermined value, having industrial applicability.

DESCRIPTION OF SYMBOLS

11: Gas supply means,
12: Regulator,
21, 21A, 21B: Liquid supply means,
22, 22A, 22B: Manometer,
31: Gas mist supply means,
32: Fluid nozzle,
51: Control device,
61: Manometer,
62: Thermometer,
100, 200, 300, 400: Cover for the gas mist pressure bath,
101, 201, 301, 401: Pressure bath cover main body,
102, 102A, 102B, 102C, 102D, 202, 302, 402: Living-body cover member,
103, 103A, 103B, 103C, 103D-1, 103D-2, 203, 303, 403: Adhesive part,
104, 204, 304, 404: Supply port,
105, 205, 305, 405: Exhaust port,
106, 106A, 106B, 106C, 206, 206A, 206B, 206C, 306, 406: Fixing part,
107, 207, 307, 407: Stopping belt,
107A: String,
107B: Rubber belt,
107C: Supporter,
108, 208, 308, 408: Belt stopper,
108B: Face fastener,
108C: Opening,
109, 221: Space,
204*q*, 212*a*: Check valve,
210, 310, 410: Pressurizing part,
211, 411: Gas storage,
212: Connection part,
302*a*: Front end (central part),
311: Reducing ring, and
411*a*: Reducing part.

The invention claimed is:

1. A cover for a gas mist pressure bath, in which a gas mist is prepared at a density of not less than a predetermined value by pulverizing and dissolving carbon dioxide or oxygen and liquid or a mixed gas of carbon dioxide and oxygen and the liquid, and the gas mist is sealed in the cover and directly contacted to a skin and a mucous membrane of a living-body, the cover comprising:

a living-body cover member for covering the skin and the mucous membrane of the living-body, an adhesive part provided on a circumferential margin of the living-body cover member for adhering the cover member to the skin and the mucous membrane of the living-body, a gas mist supply port communicating with the cover member for introducing the gas mist into the cover member, an outlet for exhausting air, the gas mist or the mixed gas sealed in the cover member and controlling amounts of the air, the gas mist, or the mixed gas, a fixing member for fixing the cover member on the living-body, including a pair of belts extending from an edge of the adhesive part, a pair of belt stoppers, and a pair of adjusters, each of the adjusters adjusting a length of each of the belts, and a reducing ring, wherein an end portion of the living-body cover member passes into a hole of the reducing ring, the reducing ring slides towards a center part of the living-body cover member from the end portion to reduce a vicinity of the end portion, so that a space storing the gas mist and the gas of the living-body cover member is made narrow and an inside of the living-body cover member is pressurized, and the living-body cover member forms a patch enabling to store the gas mist and the mixed gas inside thereof.

2. A cover for a gas mist pressure bath as set forth in claim 1, wherein the pair of belts comprises one selected from the group consisting of a rubber, a string, and a face fastener.

3. A cover for a gas mist pressure bath as set forth in claim 1, wherein the gas mist supply port has a check valve inside thereof.

4. A cover for a gas mist pressure bath as set forth in claim 1, wherein the gas mist supply port and the outlet are present on a side closer to the adhesive part away from the center part of the living-body cover member.

* * * * *